United States Patent [19]

Bigalli et al.

[11] Patent Number: 4,755,391
[45] Date of Patent: Jul. 5, 1988

[54] REMOVAL OF METHYLXANTHINES FROM CACAO MATERIALS

[75] Inventors: Giovanni L. Bigalli; Robert D. Houseal, Jr., both of Hershey, Pa.

[73] Assignee: Hershey Foods Corporation, Hershey, Pa.

[21] Appl. No.: 86,171

[22] Filed: Aug. 3, 1987

Related U.S. Application Data

[63] Continuation of Ser. No. 821,395, Jan. 22, 1986, abandoned.

[51] Int. Cl.$^4$ ............................................. A23G 1/00
[52] U.S. Cl. ................................... 426/427; 426/431
[58] Field of Search ................................ 426/431, 427

[56] References Cited

U.S. PATENT DOCUMENTS 1,750,795  3/1930  Defrew ............................. 426/431
3,398,091  8/1968  Greatorex .......................... 426/432
4,113,886  9/1978  Katz .................................. 426/427 X
4,390,698  6/1983  Chiovini et al. .................. 426/431 X
4,444,798  4/1984  Magnolato et al. .............. 426/427 X

FOREIGN PATENT DOCUMENTS 1328 of 1912 United Kingdom ................ 426/427

Primary Examiner—Joseph Golian
Attorney, Agent, or Firm—Paul & Paul

[57] ABSTRACT

A process is disclosed for removing substantially all of the theobromine normally present in cacao beans. The process includes a water extraction of cacao nibs at from about 45° C. to about 55° C. followed by a series of water extraction steps at from about 90° C. to about 105° C. Theobromine and caffeine are separated in the filtrates and the final methylxanthine extracted fraction is returned to the cacao nibs mass from which a methylxanthine extracted cacao liquor is obtained.

7 Claims, 3 Drawing Sheets

REMOVAL OF METHYLXANTHINES FROM CACAO MATERIALS

This application is a continuation of application Ser. No. 821,395 filed Jan. 22, 1986, now abandoned.

BACKGROUND OF THE ART

For some time it has been well-known that cacao beans contain a small amount of caffeine (1,3,7 trimethylxanthine) and a considerably larger amount of theobromine (3,7 dimethylxanthine). The relationship, depending upon the particular variety of cacao bean, ranges from about a ratio of two to one theobromine to caffeine to about ten to one theobromine to caffeine. Moreover, it has been found that theobromine is about 100 times less soluble in water than caffeine. The effective removal of these methylxanthines from cacao beans, therefore, must deal primarily with processes which will remove a large percentage of the relatively insoluble theobromine while at the same time removing the relatively smaller amounts of the more soluble caffeine. The present invention is directed to an improved process for the treatment of cacao beans or cacao nibs to remove methylxanthines consisting of theobromine and caffeine. Such xanthines are members of a broader chemical class known as purines. The purine system is composed of a pyrimidine ring and an imidazole ring fused together. The rings of the purine molecule are numbered starting with the nitrogen atom at the upper left corner of the pyrimidine ring and proceeding counterclockwise to the number 6 position and then proceeding clockwise from the pyrimidine number 5 position to give the 7, 8 and 9 positions in the imidazole ring. The dihydroxy purines are known as xanthines and are numbered in the same way. This nomenclature system is used throughout the present specification.

Various methods for accomplishing the removal of such methylxanthines from cacao material have been proposed heretofore. One such prior process involves the extraction of these methylxanthines by use of chlorinated hydrocarbon solvents, such as chloroform, ethylene dichloride or tetrachlorethane. Such solvent extraction processes are shown in U.S. Pat. Nos. 1,073,441, 1,855,026 and 1,925,326, respectively. However, the use of such extraction solvents is not recommended, particularly where food products are involved, since residues of such solvents are undesirable in a food product. Another method of removing theobromine from cacao beans involves extraction with water and then treating the aqueous extract with an adsorbent in subdivided form. While this method does not involve the use of objectionable chemicals, such as chlorinated hydrocarbon solvents, there are certain difficulties connected with the use of such adsorbent materials which adversely affect the taste of the final depurinized cacao product. Moreover, the percentage removal of theobromine is limited.

Still another prior process for extracting methylxanthines from cacao material comprises contacting the cacao material, swollen by treatment with a relatively small amount of water, with a food-acceptable solvent gas such as supercritical nitruns oxide or supercritical carbon dioxide. However, this process requires long treatment times and frequently does not achieve a sufficient percentage reduction in the theobromine content. Moreover, the removal of the methylxanthines from the supercritical gas presents a problem where, as is usually the case, it is desired to re-use the supercritical gas.

Still another process for removing caffeine from coffee is disclosed in U.S. Pat. No. 4,474,821 in which a countercurrent extraction process using a plurality of extraction vessels in the countercurrent operation is disclosed. However, in the process of this patent an extraction solvent consisting of ethyl acetate plus water is employed in which the ethyl acetate-water azeotrope is ultimately removed by differential pressure steam stripping. In the process of this patent turbulent flow of the extracting solvent is used to obtain an accelerated decaffeination rate which, in turn, reduces the caffeine extraction time. This prior process, as well as other extraction processes which utilize organic solvents, has the disadvantage of requiring that most of the product mass or water extract be exposed to the solvent.

DESCRIPTION OF THE INVENTION

Figure 1:
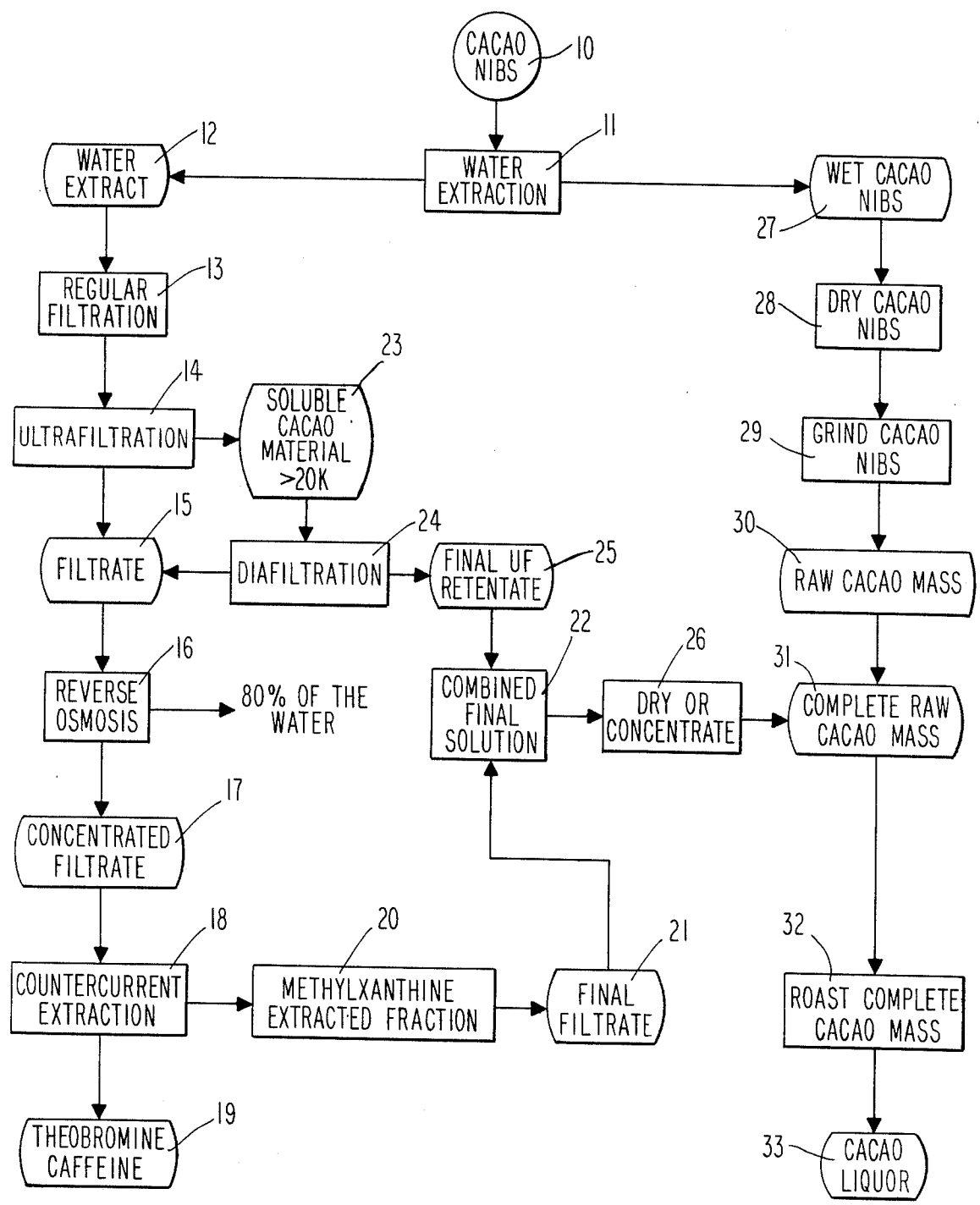
FIG. 1 consists of a flow chart showing one method for practicing the process of this invention.

The present invention is directed to a process for removing substantially all of the methylxanthines present in cacao material without employing any steps which adversely affect the depurinized final product and which minimize the amount of the final product which is exposed to organic solvents. We have discovered that extraction of cacao material with water heated to a temperature in the range from about 40° C. to about 60° C., does not remove all of the methylxanthines present in cacao material even if such water extraction is repeated many times. This is particularly true of theobromine removal where the unremoved residual theobromine is of the order of 1% to 3%. However, we have also discovered that greatly improved theobromine removal is achieved if one or more extraction steps with water at about 45° C. to about 55° C. is followed by several extraction steps with water at about 90° C. to about 105° C. We have found that the use of such a low temperature water extraction followed by a series of significantly higher temperature water extraction steps results in a much higher percentage total theobromine removal than is obtained in using either of these extraction temperatures alone. Apparently the water extraction at about 45° C. to about 55° C. changes the content, and perhaps the structure, of the cacao nibs mixture in such a way that the subsequent series of water extraction steps at about 90° C. to about 105° C. removes residual theobromine not previously removed at either temperature alone. The use of a series of high temperature extraction steps not preceded by a low temperature extraction does not remove all of the theobromine. Likewise the use of a low temperature extraction not followed by a series of high temperature extraction steps does not remove all of the theobromine. This surprising and unexpected result is shown in tables I and II based upon data developed from water extractions of CACAO nibs using various temperatures and numbers of extraction steps. The data of these tables was used in preparing the curves of FIGS. 2 and 3, respectively, of the drawings forming a part of this application.

The data set forth in Tables I and II was obtained as follows:

EXAMPLE I

Four sets of 450 grams each of raw, winnowed and degermed cocoa nibs from a bag of uniform population were prepared. For each set the nibs were placed inside a 100 mesh stainless steel extraction thimble which was then placed in a jacketed stainless steel extraction reservoir maintained at constant temperature by an external circulating water bath. 1400 ml of water were added to the extraction reservoir and the water was agitated continuously through the cocoa nib mass by recirculating from the bottom to the top of the extractor using a recirculating pump running at a rate of about 500 ml per minute for 20 minutes. The first extraction was followed by 7 more extractions in which 1100 ml of water were added each time to restore the original volume of liquid. Each of the four sets had a specific objective as will appear from the following:

The four extraction sets were run as follows:

1-a. In the first set, all 8 extractions were carried out at 55° C.
1-b. In the second set, all 8 extractions were carried out at 95° C.
1-c. In the third set, three extractions at 55° C., were followed by 5 extractions at 95° C.
1-d. In the fourth set, three extractions at 55° C., were followed by 5 extractions at 105° C. (To achieve the 105° C., temperature the extractor was kept at a suitable positive pressure.)

The results of the four extraction procedures are set forth in Table I.

TABLE I

| Cumulative Theobromine Extracted (Gms) (Gms of Theobromine/450 Gms Cacoa Nibs) | | | | | | | |
|---|---|---|---|---|---|---|---|
| NUMBER OF EXTRACTIONS | | | | | | | |
| 1 | 2 | 3 | 4 | 5 | 6 | 7 | 8 |

| | 1 | 2 | 3 | 4 | 5 | 6 | 7 | 8 |
|---|---|---|---|---|---|---|---|---|
| 1-a | 1.31 | 2.32 | 3.12 | 3.67 | 4.07 | 4.39 | 4.63 | 4.82 |
| 1-b | 2.27 | 3.72 | 4.55 | 4.96 | 5.16 | 5.24 | 5.26 | 5.27 |
| 1-c | 1.35 | 2.37 | 3.18 | 4.49 | 5.27 | 5.65 | 5.83 | 5.91 |
| 1-d | 1.30 | 2.28 | 3.05 | 4.54 | 5.37 | 5.67 | 5.79 | 5.84 |

Figure 2:
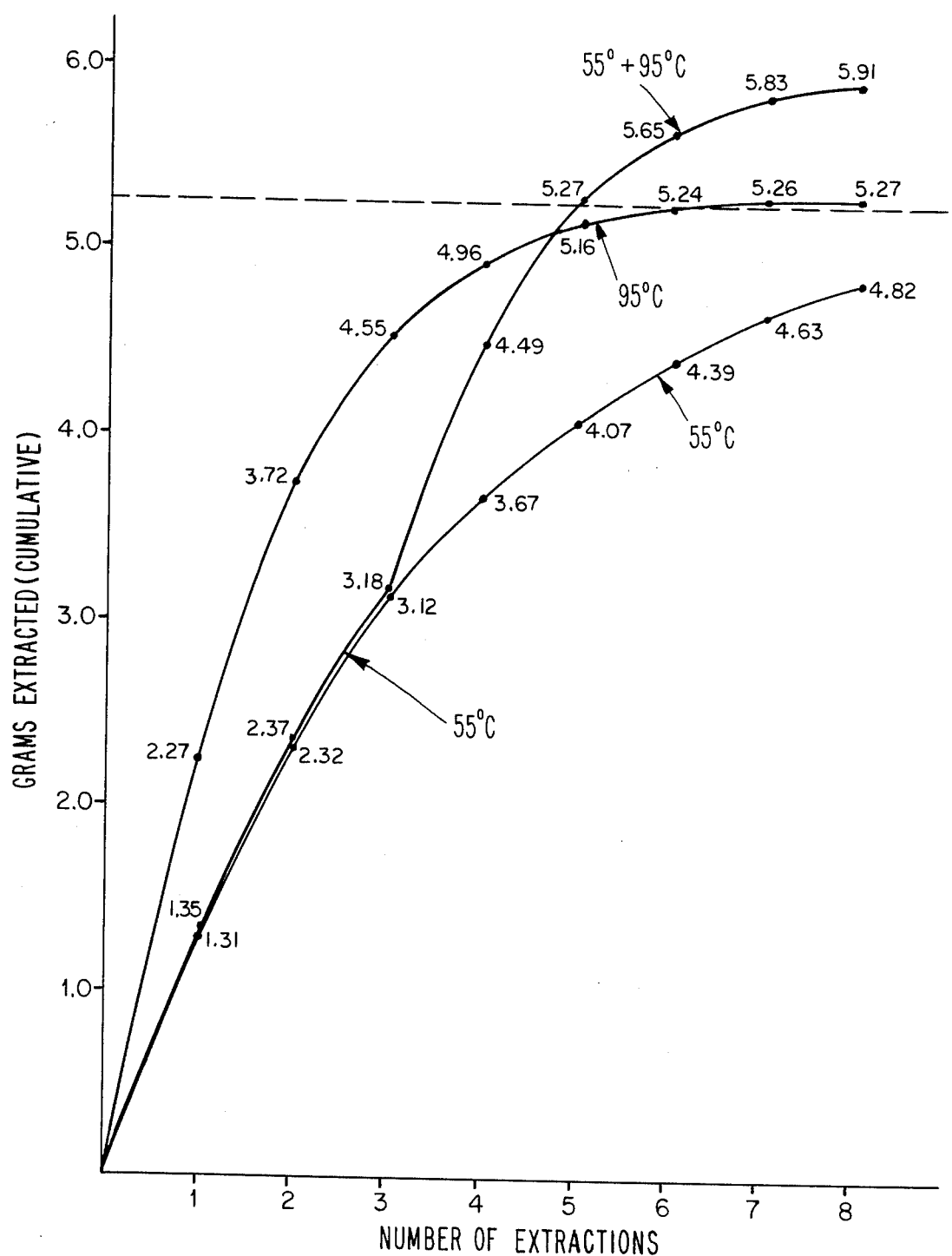
FIG. 2 consists of a series of curves in which the data set forth in Table I is depicted graphically to show low temperature, high temperature and combined low and high temperature extractions with the number of extractions plotted on the ordinate and the amount of theobromine extracted being plotted on the abscissa of a rectangular coordinate system. The temperatures applicable to each curve are indicated by means of lead lines.

The significance of the above results is apparent on examination of the curves shown in FIG. 2. The 55° C. curve shows a steady rise in the cumulative amounts of theobromine extracted, with the curve terminating well below the dashed line after 8 extractions. The dashed line represents the theoretical theobromine content obtainable using a standard AOAC analytical method. The 95° C. curve is noticeably flattened after 4 extractions and terminates substantially at the dashed line after 8 extractions. However, the curve marked 55° C. at its lower end and marked 55° C.+95° C. at its upper end terminates well above the dashed line, thus showing a substantial increase in the removal of theobromine where 3 extractions at 55° C. are followed by 5 extractions at 95° C.

EXAMPLE II

The procedures of Example I were repeated for three extraction sets and the three extraction sets were run as follows:

2-a. In the first set, one extraction at 55° C. was followed by seven extractions at 95° C.
2-b. In the second set, two extractions at 55° C. were followed by six extractions at 95° C.
2-c. In the third set, three extractions at 55° C. were followed by five extractions at 95° C.

The results of the three extractions procedures are set forth in Table II.

TABLE II

| Cumulative Theobromine Extracted (Gms) (Gms of Theobromine/450 Gms Cacoa Nibs) | | | | | | | |
|---|---|---|---|---|---|---|---|
| NUMBER OF EXTRACTIONS | | | | | | | |

| | 1 | 2 | 3 | 4 | 5 | 6 | 7 | 8 |
|---|---|---|---|---|---|---|---|---|
| 2-a | 1.31 | 3.17 | 4.43 | 5.07 | 5.40 | 5.55 | 5.61 | 5.64 |
| 2-b | 1.26 | 2.21 | 3.81 | 4.79 | 5.29 | 5.53 | 5.63 | 5.67 |
| 2-c | 1.35 | 2.37 | 3.18 | 4.49 | 5.27 | 5.65 | 5.85 | 5.91 |

The number of extractions could be 1 and 7, or 2 and 6, or 3 and 5 with comparable results. Acceptable results are obtained provided the first extraction temperature was no higher than about 55° C. and no lower than about 45° C.

EXAMPLE III

The procedures of Example I were repeated for seven extraction sets and the seven extraction sets were run as follows:

3-a. In the first set, 3 extractions at 40° C. were followed by 5 extractions at 95° C.
3-b. In the second set, 3 extractions at 50° C. were followed by 5 extractions at 95° C.
3-c. In the third set, 3 extractions at 55° C. were followed by 5 extractions at 95° C.
3-d. In the fourth set, 3 extractions at 60° C. were followed by 5 extractions at 95° C.
3-e. In the fifth set, 3 extractions at 70° C. were followed by 5 extractions at 95° C.
3-f. In the sixth set, 3 extractions at 80° C. were followed by 5 extractions at 95° C.
3-g. In the seventh set, 8 extractions were made at 95° C., each.

The results of the seven extraction procedures are set forth in Table III.

TABLE III

| Cumulative Theobromine Extracted (Gms) (Gms of Theobromine/450 Gms Cacoa Nibs) | | | | | | | |
|---|---|---|---|---|---|---|---|
| NUMBER OF EXTRACTIONS | | | | | | | |

| | 1 | 2 | 3 | 4 | 5 | 6 | 7 | 8 |
|---|---|---|---|---|---|---|---|---|
| 3-a | 0.81 | 1.44 | 1.93 | 3.49 | 4.46 | 4.99 | 5.26 | 5.41 |
| 3-b | 1.26 | 2.19 | 2.95 | 4.43 | 5.31 | 5.78 | 5.99 | 6.09 |
| 3-c | 1.40 | 2.41 | 3.22 | 4.47 | 5.27 | 5.68 | 5.89 | 5.98 |
| 3-d | 1.45 | 2.56 | 3.42 | 4.49 | 5.17 | 5.54 | 5.73 | 5.82 |
| 3-e | 1.72 | 2.96 | 3.82 | 4.71 | 5.23 | 5.50 | 5.64 | 5.71 |
| 3-f | 2.03 | 3.40 | 4.25 | 4.90 | 5.26 | 5.45 | 5.55 | 5.59 |
| 3-g | 2.28 | 3.78 | 4.62 | 5.03 | 5.23 | 5.32 | 5.36 | 5.37 |

Figure 3:
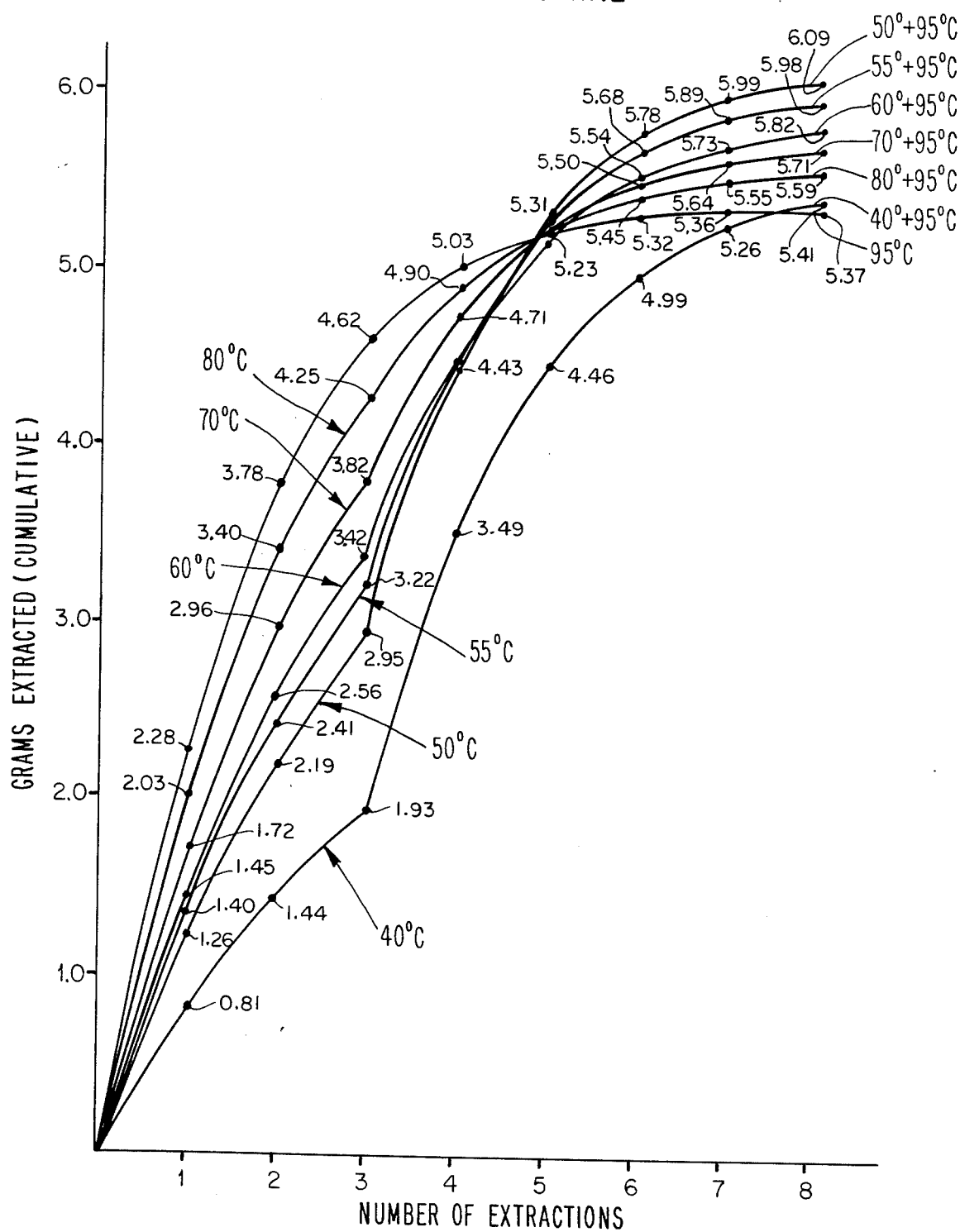
FIG. 3 consists of a series of curves in which the data set forth in Table III is depicted graphically to show the effects of dual temperature extraction systems operating at various initial stage temperatures.

The significance of the above results is apparent on examination of the curves shown in FIG. 3. In this figure each of the plotted points is marked with a number indicating the cumulative amount in grams of the theobromine extracted. The temperatures for each of the curves are also indicated. In each case except for the 95° C. curve there are two temperatures shown. The first temperature applies to the lower portion (3 extractions) of the particular curve and the second temperature applies to the upper portion (an additional 5 extractions). The experiment illustrates that the maximum extraction occurs when the initial temperature is 50°±5°.

PREFERRED CONDITIONS FOR PRACTICING THE INVENTION

A convenient starting point (10) (FIG. 1) for the practice of the process of the present invention consists of preparing a quantity of raw cacao nibs obtained from cacao beans, using standard and well-known procedures. Practically speaking, the process of the present invention consists of a series of water extraction steps that separate substantially all the water soluble materials, including caffeine and theobromine, from the original raw cacao nibs, thereby producing a water extract of the cacao nibs and a quantity of wet cacao nibs. This water extraction is carried out in a series of steps at two quite different temperatures: (1) the nibs are first extracted with water about 45° C. to about 55° C. (2) This is followed by extraction with water about four or five times at about 90° C. to about 105° C. After each extraction substantially all of the liquid is drained out of the extraction vessel and water is then added.

The wet cacao nibs (27) remaining after the water extraction steps, now deprived of substantially all methylxanthines and most water soluble materials, are dried slowly (28). When the moisture in the nibs reaches a point below about 4 percent they are stored and eventually ground (29) to obtain a product known as raw cocoa mass (30). In order to obtain a pumpable liquid, the mass is reground. This reground raw cocoa mass (31) is then ready to be blended with the solids of the water soluble material (26) which were extracted from the nibs initially.

The water extract resulting from the extraction steps is filtered in a filter press (13) or in a centrifugal clarifier to eliminate small particles. The filtered extract is then submitted to an ultrafiltration step (14) using separation membranes having a cut-off molecular weight of about 10,000 or about 20,000. The filtrate (15) from the membrane will contain more than 97 percent of the water originally present in the water extract and will contain caffeine, theobromine and molecules smaller than the cut-off value of the membrane. The material remaining is an ultrafiltration retentate (23) which contains soluble cacao material greater than molecular weight 20,000. The water will be no more than 3 percent of the original volume and will contain very small amounts of caffeine and theobromine.

The small amounts of the two major methylxanthines that remain in the retentate, namely dimethylxanthine and trimethylxanthine, are minimized by diafiltration (24) which is carried out by adding an equal volume (3 percent of the original) of water to the retentate. Then another equal volume of water is added and the process of diafiltration (24) is repeated at least four times. The filtrate of the diafiltration steps is added to the main filtrate (15). The final volume of the filtrate is from about 109-115 percent of the original volume of the extract. The retentate, containing about 10 percent cacao solids, is concentrated in an evaporator until the original is reduced to about ½ or ⅓ by volume. This solution, which is called Final UF Retentate (25) is now in a condition suitable for further processing.

The material remaining after the filtration step (15) contains water-soluble substances of molecular weight less than 20,000 and is subjected to a concentration process (16) in which at least 80 percent of the water contained is eliminated by reverse osmosis which is a known physical procedure commercially available for concentration of solids and for desalinization of sea water. The concentrated filtrate (17) which contains caffeine, theobromine, cacao solids and water soluble, low molecular weight substances is submitted to a countercurrent extraction (18) with methylene chloride. This countercurrent extraction is based on the partition coefficient of the two methylxanthines between the water and the methylene chloride. The methylene chloride is recirculated and redistilled at a constant rate in such a way that it circulates in the partition column from top to bottom taking advantage of the specific gravity of the methylene chloride solvent. The partition column used in the countercurrent extraction step is maintained at a temperature of about 30° C. to about 38° C. The concentrated filtrate is pumped into the partition column from the bottom at a rate equal to the distillation rate of the methylene chloride. In order to obtain a removal of caffeine better than 97 percent, 6 volumes of methylene chloride must be redistilled for each volume of concentrated filtrate while 18 volumes are needed for the same efficiency in the case of the extraction of theobromine. This result is obtainable by increasing the number of reactive columns in series, by recycling the concentrated filtrate into the same columns as needed or by decreasing proportionately the speed of the flow of the concentrated filtrate.

The concentrated filtrate, resulting from the countercurrent extraction, is now in the form of a methylxanthine extracted fraction (20). The caffeine and theobromine (19) are recovered at a high level of purity from an evaporator following the methylene chloride extraction step. The methylxanthine extracted fraction (20) is then evaporated under reduced pressure which substantially eliminates all small residues of solvent. Evaporation is continued until the solids reach about 10 percent by volume. This concentrated material is designated as the Final Filtrate (21).

The Final Filtrate and the Final UF Retentate (25) are now combined (22). The combined final solution is then dried (26) by a conventional drying technique such as freeze drying or spray drying. The powder thus obtained is added to the reground raw cacao mass (31) which is then roasted in a cacao mass roaster (32) of known design.

A second alternative is to concentrate the combined final solution (22) and inject it directly into a cacao mass reactor. The solution is added in several steps, thus evaporating the water prior to the roasting of the complete cacao mass in the same reactor. The roasted cacao mass is equivalent to conventional cacao liquor in quality, flavor and functionality but is substantially free of xanthine stimulants, particularly theobromine.

The above over-all process description is provided in order to illustrate one way of utilizing the multi-stage extraction process of the present invention.

We claim:

1. A process for removing theobromine and caffeine from cacao beans consisting essentially of the steps of subjecting cacao nibs to a low temperature water extraction at temperatures from about 45° C. to about 55° C. followed by a series of high temperature water extraction steps at temperatures from about 90° C. to about 105° C., said low temperature and high temperature water extraction steps comprising the ratio of 1100 ml of water per 450 grams of cacao nibs, removing the extraction filtrates and then recovering cacao liquor substantially free of theobromine and caffeine from the cacao mass thus obtained.

2. The process of claim 1 further characterized by including at least one water extraction step in the low temperature set of extractions and at least three water extraction steps in the high temperature set of extractions.

3. The process of claim 2 further characterized by carrying out the low temperature extraction at about 55° C. and carrying out the high temperature extraction steps at about 95° C.

4. The process of claim 1 further characterized by the steps of subjecting the removed extraction filtrates to ultrafiltration and diafiltration to obtain an ultrafiltration retentate and then adding said retentate to the cacao mass prior to recovering the theobromine and caffeine extracted cacao liquor from the cacao mass.

5. The process of claim 1 further characterized by the steps of removing methylxanthines from the extraction filtrate and then adding the methylxanthine extracted fraction thus obtained to said cacao mass prior to processing into cacao liquor from the cacoa mass.

6. The process of claim 4 further characterized by subjecting the extraction filtrate from the ultrafiltration and diafiltration steps to concentration and countercurrent extraction steps and then adding said methylxanthine extracted fraction to the cacao mass prior to processing into cacao liquor from the cacao mass.

7. The process of claim 6 further characterized by carrying out the concentration step by reverse osmosis.

* * * * *